US012735405B2

(12) United States Patent
Chen et al.

(10) Patent No.: US 12,735,405 B2
(45) **Date of Patent: *Sep. 15, 2026**

(54) METHOD FOR PREPARING BILIVERDIN OR DERIVATIVE THEREOF

(71) Applicant: WUHAN JIANMIN DAPENG PHARMACEUTICAL CO., LTD., Hubei (CN)

(72) Inventors: Fapu Chen, Wuhan (CN); Yuxin Shi, Wuhan (CN); Fakai Chen, Wuhan (CN)

(73) Assignee: WUHAN JIANMIN DAPENG PHARMACEUTICAL CO., LTD., Hubei (CN)

( * ) Notice: Subject to any disclaimer, the term of this patent is extended or adjusted under 35 U.S.C. 154(b) by 512 days.

This patent is subject to a terminal disclaimer.

(21) Appl. No.: 18/206,653

(22) Filed: Jun. 7, 2023

(65) Prior Publication Data

US 2023/0312533 A1 Oct. 5, 2023

Related U.S. Application Data

(63) Continuation-in-part of application No. PCT/CN2021/073781, filed on Jan. 26, 2021.

(30) Foreign Application Priority Data

Dec. 22, 2020 (CN) ........................ 202011529380.X

(51) Int. Cl.

| | |
|---|---|
| ***C07D 403/14*** | (2006.01) |
| ***B01J 31/02*** | (2006.01) |
| ***C07D 207/44*** | (2006.01) |

(52) U.S. Cl.
CPC ........ *C07D 403/14* (2013.01); *B01J 31/0204* (2013.01); *B01J 31/0235* (2013.01); *C07D 207/44* (2013.01)

(58) Field of Classification Search
CPC ............................ C07D 403/14; C07D 207/44
See application file for complete search history.

(56) References Cited

FOREIGN PATENT DOCUMENTS

CN 109535057 A * 3/2019 ........... C07D 207/44

OTHER PUBLICATIONS

Sturrock et al., “The Synthesis of [10-13C]Bilirubin IXa”, 1994, Journal of Labelled Compounds and Radiopharmaceuticals, 34, pp. 263-274 (Year: 1994).*
PhysicsOpenLab, “Porphyrins: The Colors of Life”, 2016, physicsopenlab.org, 9 pages (Year: 2016).*
PubChem, “3,8, 13,18-Tetrakis(carboxymethyl)-5,10,15,22,23,24-hexahydro-19-(hydroxymethyl)-21H-biline-2,7,12, 17-tetrapropanoic acid”, 2004, National Library of Medicine, 25 pgs. (Year: 2004).*
CAPLUS, RN 2630389-66-9, 2021, STN, 1 pg. (Year: 2021).*

* cited by examiner

*Primary Examiner* — Brenda L Coleman
*Assistant Examiner* — Madeline E Braun
(74) *Attorney, Agent, or Firm* — JCIP GLOBAL INC.

(57) ABSTRACT

A method for preparing biliverdin or a derivative thereof includes applying a compound represented by formula 2 as a raw material; R is hydrogen, $C_1$-$C_5$ alkyl, or benzyl; “---” at positions A and B independently represent a single bond or a double bond; when “---” represents a single bond, $R_1$ or $R_2$ connected to the single bond is selected from one of tosyl, p-toluenesulfonyl, phenylsulfonyl, phenylsulfinyl; and when “---” represents a double bond, $R_1$ or $R_2$ connected to the double bond is hydrogen.

2 Claims, No Drawings

METHOD FOR PREPARING BILIVERDIN OR DERIVATIVE THEREOF

CROSS-REFERENCE TO RELATED APPLICATIONS

This application is a continuation-in-part of International Patent Application No. PCT/CN2021/073781 with an international filing date of Jan. 26, 2021, designating the United States, now pending, and further claims foreign priority benefits to Chinese Patent Application No. 202011529380.X filed Dec. 22, 2020. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, MA 02142.

BACKGROUND

The disclosure relates to the field of synthesis of pharmaceuticals, and more particularly to a method for preparing biliverdin or a derivative thereof.

Biliverdin is a tetrapyrrole compound (its structure is shown in Formula 8) obtained from the hydrolysis of heme by hemeoxygenase-1 (HO-1). Biliverdin is an intermediate of metabolism and circulation of heme, and can initiate physiological functions such as anti-inflammatory and immune regulation, to improve liver function, reduce alanine transaminase, alleviate ischemia reperfusion injury caused by liver transplantation, inhibit vascular remodeling caused by the formation of new tunica intima, and inhibit replication of bovine diarrhea virus. Therefore, biliverdin has great potential for clinical drug use.

In addition, bilirubin IXα is a main raw material for in vitro cultivation of bezoar. Biliverdin IXα can be used to prepare bilirubin IXα, and biliverdin IXα is also an important pharmaceutical intermediate.

At present, the preparation of biliverdin mainly includes extraction, chemical conversion, enzymatic conversion and biosynthesis. Due to the limited source of raw materials and the easy formation of multiple isomers during the extraction process of bilirubin, the yield and purity of the product bilirubin are low. Conventionally, biliverdin is prepared by chemical oxidation of heme, which produces more isomers with lower yield than other methods. At present, there are reports on the conversion of biliverdin from heme by enzymatic conversion and biosynthesis, but the selectivity of oxidative ring opening is not high, and the source of heme is limited, the price is high, so the method is not suitable for industrial production.

Formula 8

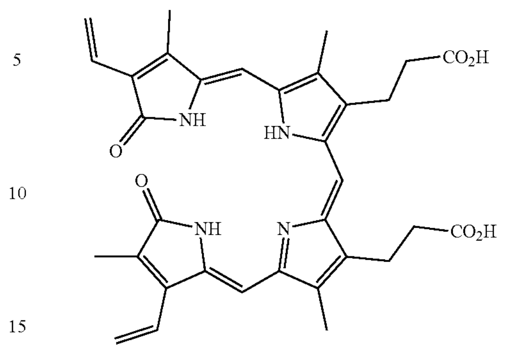

Preparation of biliverdin and bilirubin through synthetic method is an important and effective way. The method uses 3,3'-(3,18-dichloroethyl-2,7,13,17-tetramethyl-1,19-dioxo-1,19,22,24-tetrahydro-21H-8,12-porphyrinyl)-dipropionate dimethyl ester as raw material, and removes hydrogen chloride under strong alkaline conditions to obtain biliverdin dimethyl ester. However, this method involves complex steps, with low yield and high cost. The dehydrochlorination reaction is performed under strong alkaline conditions to produce biliverdin dimethyl ester and a 3-position and 18-position cyclization product with a molar ratio of about 1:1. The yield of biliverdin is low, only 20%. In addition, biliverdin dimethyl ester and the 3-position and 18-position cyclization product need to be separated by chromatography, which is not suitable for industrial production.

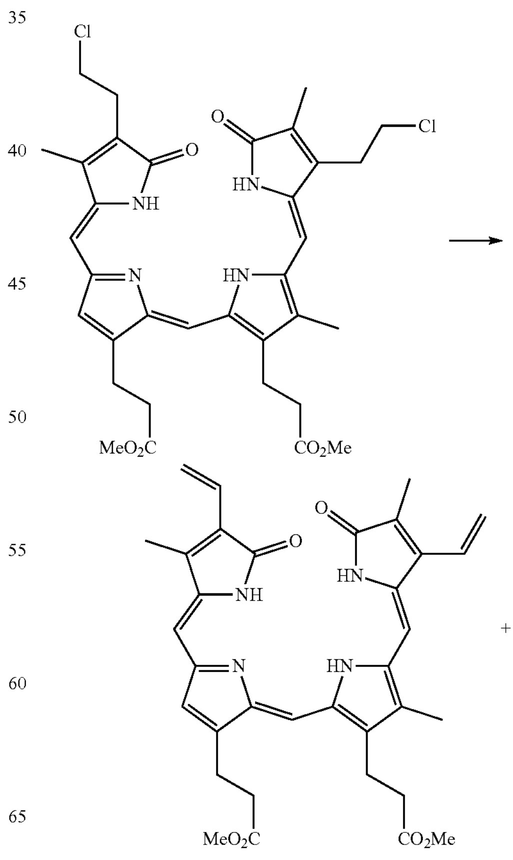

-continued

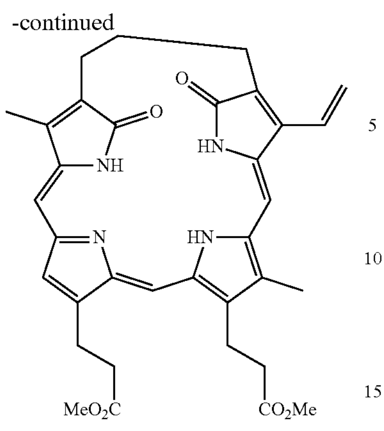

Therefore, it is necessary to find a short preparation method of biliverdin or its derivatives that does not require chromatographic separation and is suitable for industrial production.

SUMMARY

To solve the aforesaid problems, the disclosure provides a method for preparing biliverdin or a derivative thereof, the method comprising applying a compound represented by formula 2 as a raw material:

2

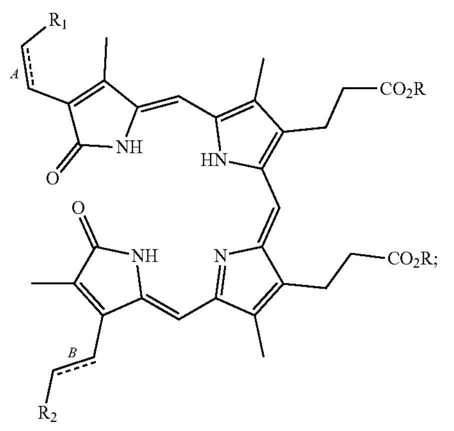

where, R is hydrogen, $C_1$-$C_5$ alkyl, or benzyl; "---" at positions A and B independently represents a single bond or a double bond; when "---" represents a single bond, $R_1$ or $R_2$ connected to the single bond is selected from one of Tosyl, p-toluenesulfonyl, phenylsulfonyl, phenylsulfinyl; and when "---" represents a double bond, $R_1$ or $R_2$ connected to the double bond is hydrogen.

In a class of this embodiment, the biliverdin or a derivative thereof has a formula 1 as follows:

1

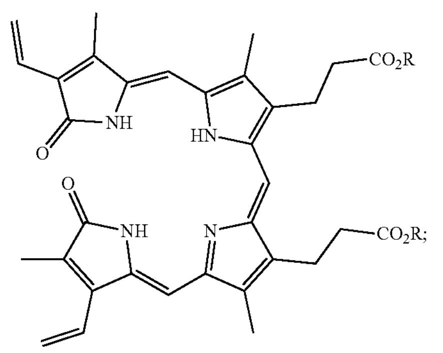

R is hydrogen, $C_1$-$C_5$ alkyl, or benzyl.

In a class of this embodiment, the compound represented by formula 2 is one of the following compounds.

3

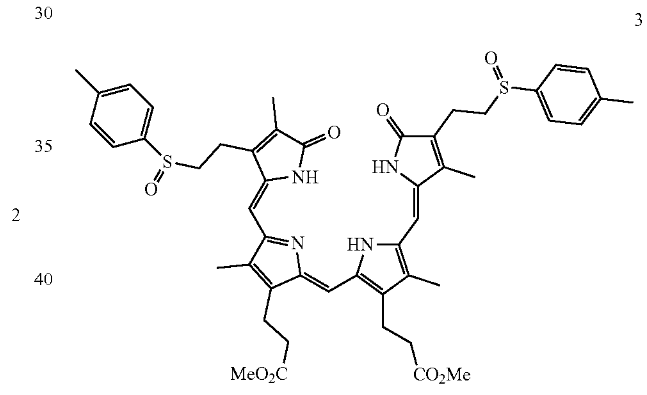

4

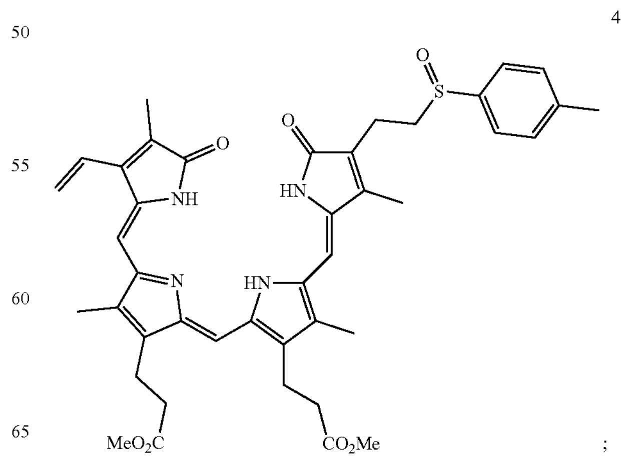

;

-continued

5

6

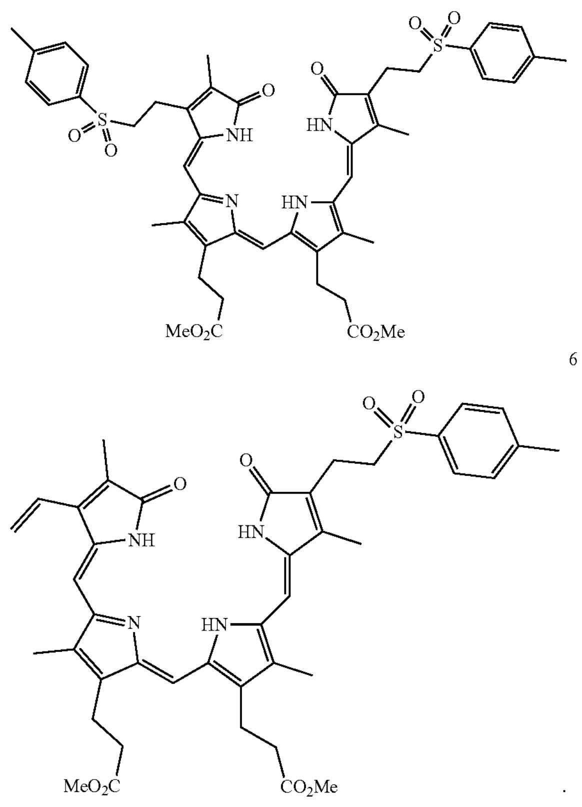

In a class of this embodiment, the biliverdin or a derivative thereof is prepared by the compound represented by formula 2 through a heating reaction.

In a class of this embodiment, the heating reaction involves a solvent selected from substituted benzene, pyrrolidone, dimethyl formamide (DMF), and tetrahydrofuran (THF), or a mixture thereof, and a yield of a final product is no less than 45%.

In a class of this embodiment, the solvent is selected from xylene, nitrobenzene, chlorobenzene, DMF, THF, or a mixture thereof.

In a class of this embodiment, the heating reaction is performed at a temperature of 100-160° C.; under the condition, the yield of a final product is more than 45%.

In a class of this embodiment, the heating reaction is performed at a temperature of 130-150° C.; under the condition, the yield of a final product is more than 60%.

In a class of this embodiment, the biliverdin or a derivative thereof is prepared by the compound represented by formula 2 in the presence of a catalyst.

In a class of this embodiment, the catalyst is an organic base. When the organic base is added as a catalyst in the reaction system and the reaction temperature is controlled between 130 and 150° C., the reaction yield can reach 70% or more in the presence of an appropriate solvent.

In a class of this embodiment, the organic base is pyridine, sodium ethoxide, or a mixture thereof, and the reaction yield can reach no less than 73%.

In a class of this embodiment, after reaction, the biliverdin or its derivatives are extracted by recrystallization.

In a class of this embodiment, the solvent used in the recrystallization is ethyl acetate, ethanol, or a mixture thereof.

In a class of this embodiment, after reaction, the biliverdin or its derivatives are extracted by dichloromethane after acidification.

The following advantages are associated with the method for preparing biliverdin or a derivative thereof of the disclosure:

1. The preparation method of biliverdin or its derivatives is easy to operate, does not require column chromatography, with high yield and low cost, and is suitable for industrial production;
2. The preparation method of biliverdin or its derivatives reduces the generation of by-products similar to the final product in the synthesis of biliverdin dimethyl ester or biliverdin, so the product is easy to purify, thus improving the purity of the product.

DETAILED DESCRIPTION

To further illustrate the disclosure, embodiments detailing a method for preparing biliverdin or a derivative thereof are described below. It should be noted that the following embodiments are intended to describe and not to limit the disclosure. If no specific technology or conditions are stated in the disclosure, the technology or conditions described in the related art or the product manual should be followed. Nuclear magnetic resonance (NMR) was measured using Bruker-AMX400 nuclear magnetic resonance instrument. ESI-MS was measured using Finnigan-MAT-95 mass spectrometer. All reagents are analytical pure (Sinopharm Chemical Reagent Co., Ltd.). In the following examples, 1,5-dihydro-4-methyl-3-(2-p-toluenesulfoethyl)-5-p-toluenesulfonyl-2H-2-pyrrolidone (shown in Formula 12) is prepared in reference to Chem Lett., 2001, 6, 590-591; 5-formyl-3-methoxycarbonyleth-4-methylpyrrolic acid tert butyl ester (shown in Formula 13), 9-tert-butoxycarbonyl-3,7-dimethyl-8-(2-methoxycarbonyleth)-2-(2-p-toluenesulfonyl ethyl)-dipyrrolomethen-1-one (shown in Formula 17) are prepared in reference to Bull. Chem. Soc. Jpn., 1994, 67, 3088-3093; 9-formyl-2,7-dimethyl-8-(2-methoxycarbonyl ethyl)-3-(2-p-tolylene sulfinyl ethyl)-dipyrrolidone 1-one (shown in Formula 14), 9-tert-butyloxycarbonyl-2,7-dimethyl-8-(2-methoxycarbonyl ethyl)-3-(2-p-tolylene thioethyl)-dipyrrolidone 1-one (shown in Formula 18) are prepared in reference to J. Org. Chem., 2020, 85, 13015-13028; 9-formyl-2,7-dimethyl-8-(2-methoxycarbonylethyl)-3-vinyldipyrrolidene-1-one (shown in formula 15) is prepared in reference to Angew. Chem. Int. Ed., 1998, 37, 13-14, 1843-1846.

Example 1

0.92 g of compound 21H-Biline-8,12-dipropanoic acid, 1,19,22,24-tetrahydro-2,7,13,17-tetramethyl-{3,18-bis-[2-[(4-methylphenyl)sulfinyl]ethyl]}-1,19-dioxo-8,12-dimethyl ester (shown in Formula 3) was dissolved in 40 mL of xylene. The resulting mixture was heated to 135° C. and stirred for 2 hours, cooled, evaporated to remove the solvent under reduced pressure, and the residue was recrystallized with ethyl acetate to obtain 0.50 g of a blue-green solid, which was biliverdin diester (shown in formula 7), with a yield of 63%. $^1H$ NMR (400 MHz, $CDCl_3$): δ1.89 (s, 3H), 2.10 (s, 3H), 2.13 (s, 3H), 2.20 (s, 3H), 2.56 (t, J=8.1 Hz, 4H), 2.95 (t, J=8.1 Hz, 4H), 3.69 (s, 6H), 5.46 (d, J=12.0 Hz, 1H), 5.66 (dd, J=12.0, 4.0 Hz, 1H), 5.68 (dd, J=16.0, 4.0 Hz, 1H), 6.02 (s, 1H), 6.08 (s, 1H), 6.14 (dd, J=16.0, 4.0 Hz, 1H), 6.51 (dd, J=16.0, 12.0 Hz, 1H), 6.64 (dd, J=16.0, 12.0 Hz, 1H), 6.81 (s, 1H); ESI-Mass: 633.20 $(M+Na)^+$.

The reaction formula is as follows:

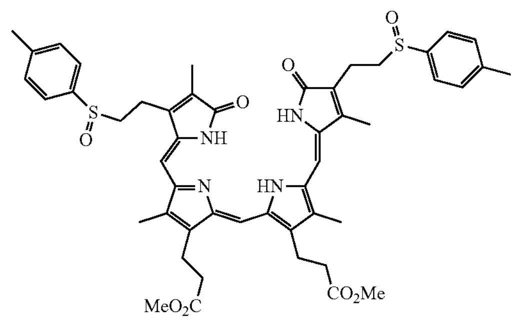

Formula 3

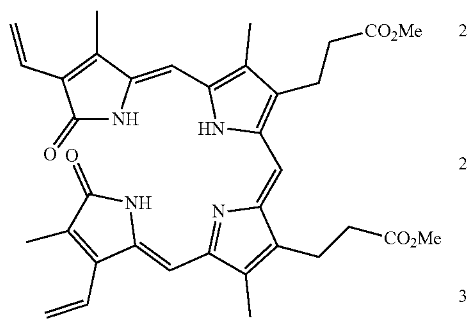

Formula 7

Example 2

0.92 g of 21H-Biline-8,12-dipropanoic acid,3-ethenyl-1,19,22,24-tetrahydro-2,7,13,17-tetramethyl-18-[2-[(4-methylphenyl)sulfinyl]ethyl]-1,19-dioxo-8,12-dimethyl ester (shown in Formula 4) was dissolved in 40 mL of DMF. The resulting mixture was heated to 130° C. and stirred for 2 hours, cooled, evaporated to remove the solvent under reduced pressure, and the residue was recrystallized with ethyl acetate to obtain a blue-green solid, which was biliverdin diester (shown in formula 7), with a yield of 60%.

The reaction formula is as follows:

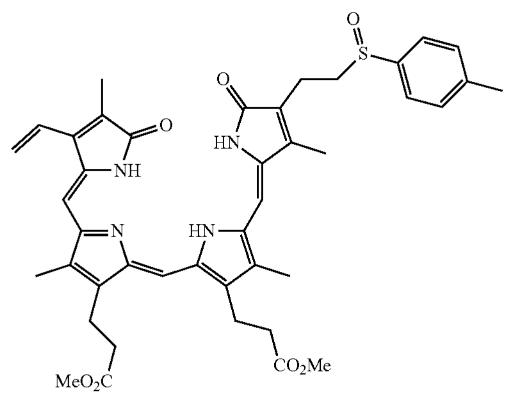

Formula 4

-continued

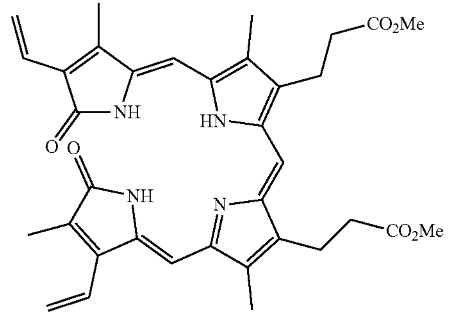

Formula 7

Example 3

0.92 g of compound 21H-Biline-8,12-dipropanoic acid, 1,19,22,24-tetrahydro-2,7,13,17-tetramethyl-{3,18-bis-[2-[(4-methylphenyl)sulfinyl]ethyl]}-1,19-dioxo-8,12-dimethyl ester (shown in formula 3) was dissolved in 40 mL of nitrobenzene. The resulting mixture was heated to 150° C. and stirred for 2 hours, cooled, evaporated to remove the solvent under reduced pressure, and the residue was recrystallized with ethyl acetate to obtain 0.50 g of a blue-green solid, which was biliverdin diester (shown in formula 7), with a yield of 61%. $^{1}H$ NMR (400 MHz, $CDCl_3$): δ1.89 (s, 3H), 2.10 (s, 3H), 2.13 (s, 3H), 2.20 (s, 3H), 2.56 (t, J=8.1 Hz, 4H), 2.95 (t, J=8.1 Hz, 4H), 3.69 (s, 6H), 5.46 (d, J=12.0 Hz, 1H), 5.66 (dd, J=12.0, 4.0 Hz, 1H), 5.68 (dd, J=16.0, 4.0 Hz, 1H), 6.02 (s, 1H), 6.08 (s, 1H), 6.14 (dd, J=16.0, 4.0 Hz, 1H), 6.51 (dd, J=16.0, 12.0 Hz, 1H), 6.64 (dd, J=16.0, 12.0 Hz, 1H), 6.81 (s, 1H); ESI-Mass: 633.20 $(M+Na)^{+}$.

Example 4

0.92 g of compound 21H-Biline-8,12-dipropanoic acid, 1,19,22,24-tetrahydro-2,7,13,17-tetramethyl-{3,18-bis-[2-[(4-methylphenyl)sulfinyl]ethyl]}-1,19-dioxo-8,12-dimethyl ester (shown in formula 3) was dissolved in 40 mL of pyrrolidone. The resulting mixture was heated to 135° C. and stirred for 2 hours, cooled, evaporated to remove the solvent under reduced pressure, and the residue was recrystallized with ethyl acetate to obtain 0.50 g of a blue-green solid, which was biliverdin diester (shown in formula 7), with a yield of 45%. $^{1}H$ NMR (400 MHz, $CDCl_3$): δ1.89 (s, 3H), 2.10 (s, 3H), 2.13 (s, 3H), 2.20 (s, 3H), 2.56 (t, J=8.1 Hz, 4H), 2.95 (t, J=8.1 Hz, 4H), 3.69 (s, 6H), 5.46 (d, J=12.0 Hz, 1H), 5.66 (dd, J=12.0, 4.0 Hz, 1H), 5.68 (dd, J=16.0, 4.0 Hz, 1H), 6.02 (s, 1H), 6.08 (s, 1H), 6.14 (dd, J=16.0, 4.0 Hz, 1H), 6.51 (dd, J=16.0, 12.0 Hz, 1H), 6.64 (dd, J=16.0, 12.0 Hz, 1H), 6.81 (s, 1H); ESI-Mass: 633.20 $(M+Na)^{+}$.

Example 5

0.92 g of compound 21H-Biline-8,12-dipropanoic acid, 1,19,22,24-tetrahydro-2,7,13,17-tetramethyl-{3,18-bis-[2-[(4-methylphenyl)sulfinyl]ethyl]}-1,19-dioxo-8,12-dimethyl ester (shown in formula 3) was dissolved in 40 mL of xylene. The resulting mixture was heated to 100° C. and stirred for 2 hours, cooled, evaporated to remove the solvent under reduced pressure, and the residue was recrystallized with ethyl acetate to obtain 0.50 g of a blue-green solid, which was biliverdin diester (shown in formula 7), with a yield of 51%. $^{1}H$ NMR (400 MHz, $CDCl_3$): δ1.89 (s, 3H), 2.10 (s, 3H), 2.13 (s, 3H), 2.20 (s, 3H), 2.56 (t, J=8.1 Hz, 4H), 2.95 (t, J=8.1 Hz, 4H), 3.69 (s, 6H), 5.46 (d, J=12.0 Hz, 1H), 5.66 (dd, J=12.0, 4.0 Hz, 1H), 5.68 (dd, J=16.0, 4.0 Hz, 1H), 6.02 (s, 1H), 6.08 (s, 1H), 6.14 (dd, J=16.0, 4.0 Hz, 1H), 6.51 (dd, J=16.0, 12.0 Hz, 1H), 6.64 (dd, J=16.0, 12.0 Hz, 1H), 6.81 (s, 1H); ESI-Mass: 633.20 $(M+Na)^+$.

Example 6

0.92 g of compound 21H-Biline-8,12-dipropanoic acid, 3-ethenyl-1,19,22,24-tetrahydro-2,7,13,17-tetramethyl-18-[2-[(4-methylphenyl)sulfinyl]ethyl]-1,19-dioxo-8,12-dimethyl ester (shown in formula 4) was dissolved in 40 mL of DMF. The resulting mixture was heated to 160° C. and stirred for 2 hours, cooled, evaporated to remove the solvent under reduced pressure, and the residue was recrystallized with ethyl acetate to obtain a blue-green solid, which was biliverdin diester (shown in formula 7), with a yield of 49%.

Example 7

0.92 g of compound 21H-Biline-8,12-dipropanoic acid, 1,19,22,24-tetrahydro-2,7,13,17-tetramethyl-{3,18-bis-[2-[(4-methylphenyl)sulfinyl]ethyl]}-1,19-dioxo-8,12-dimethyl ester (shown in formula 3) was dissolved in 40 mL of xylene. Thereafter, 10 mL of pyridine was added as a catalyst. The resulting mixture was heated to 135° C. and stirred for 2 hours, cooled, evaporated to remove the solvent under reduced pressure, and the residue was recrystallized with ethyl acetate to obtain 0.50 g of a blue-green solid, which was biliverdin diester (shown in formula 7), with a yield of 73%. $^1H$ NMR (400 MHz, $CDCl_3$): δ1.89 (s, 3H), 2.10 (s, 3H), 2.13 (s, 3H), 2.20 (s, 3H), 2.56 (t, J=8.1 Hz, 4H), 2.95 (t, J=8.1 Hz, 4H), 3.69 (s, 6H), 5.46 (d, J=12.0 Hz, 1H), 5.66 (dd, J=12.0, 4.0 Hz, 1H), 5.68 (dd, J=16.0, 4.0 Hz, 1H), 6.02 (s, 1H), 6.08 (s, 1H), 6.14 (dd, J=16.0, 4.0 Hz, 1H), 6.51 (dd, J=16.0, 12.0 Hz, 1H), 6.64 (dd, J=16.0, 12.0 Hz, 1H), 6.81 (s, 1H); ESI-Mass: 633.20 $(M+Na)^+$.

Example 8

0.92 g of compound 21H-Biline-8,12-dipropanoic acid, 3-ethenyl-1,19,22,24-tetrahydro-2,7,13,17-tetramethyl-18-[2-[(4-methylphenyl)sulfinyl]ethyl]}-1,19-dioxo-8,12-dimethyl ester (shown in formula 4) was dissolved in 40 mL of DMF. Thereafter, 10 mL of pyridine was added as a catalyst. The resulting mixture was heated to 130° C. and stirred for 2 hours, cooled, evaporated to remove the solvent under reduced pressure, and the residue was recrystallized with ethyl acetate to obtain a blue-green solid, which was biliverdin diester (shown in formula 7), with a yield of 74%.

Example 9

0.92 g of 21H-Biline-8,12-dipropanoic acid, 1,19,22,24-tetrahydro-2,7,13,17-tetramethyl-{3,18-bis-[2-[(4-methylphenyl)sulfinyl]ethyl]}-1,19-dioxo-8,12-dimethyl ester (shown in formula 5) was dissolved in 40 mL of anhydrous THF, and then 0.93 g of sodium tert-butoxide dissolved in 10 mL of tert-butanol was added. The resulting mixture was heated to 135° C. and stirred for 2 hours, cooled, evaporated to remove the solvent under reduced pressure. The residue was mixed with water, acidified with dilute hydrochloric acid, and extracted with dichloromethane to obtain 0.50 g of a blue-green solid, which was biliverdin (shown in Formula 8), with a yield of 74%. The spectral data is consistent with the literature Monatshr Chem., 1989, 120, 575-580.

The reaction formula is as follows:

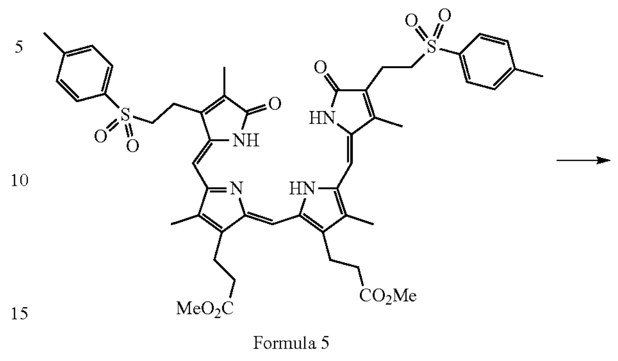

Formula 5

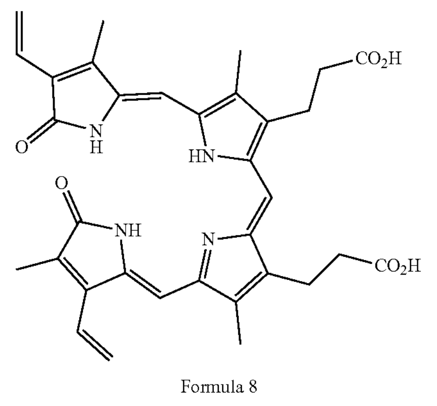

Formula 8

Example 10

0.77 g of 3,3'-(3-vinyl-18-(2-p-tolylene sulfonyl group ethyl)-2,7,13,17-tetramethyl-1,19-dioxo-1,19,22,24-tetrahydro-21H-8,12-porphyrin)-dipropionate dimethyl ester (shown in formula 6) was dissolved in 35 mL of anhydrous THF, and then 0.93 g of sodium tert-butoxide dissolved in 10 mL of tert-butanol was added. The resulting mixture was heated to 135° C. and stirred for 2 hours, cooled, evaporated to remove the solvent under reduced pressure. The residue was mixed with water, acidified with dilute hydrochloric acid, and extracted with dichloromethane to obtain 0.40 g of a blue-green solid, which was biliverdin (shown in Formula 8), with a yield of 69%. The spectral data is consistent with the literature Monatshr Chem., 1989, 120, 575-580.

0.77 g of 21H-Biline-8,12-dipropanoic acid,3-ethenyl-1,19,22,24-tetrahydro-2,7,13,17-tetramethyl-18-[2-[(4-methylphenyl)sulfonyl]-1,19-dioxo,8,12-dimethyl ester (shown in formula 6) was dissolved in 35 mL of anhydrous THF, and then 0.93 g of sodium tert-butoxide dissolved in 10 mL of tert-butanol was added. The resulting mixture was heated to 135° C. and stirred for 2 hours, cooled, evaporated to remove the solvent under reduced pressure. The residue was mixed with water, acidified with dilute hydrochloric acid, and extracted with dichloromethane to obtain 0.40 g of a blue-green solid, which was biliverdin (shown in Formula 8), with a yield of 69%. The spectral data is consistent with the literature Monatshr Chem., 1989, 120, 575-580.

The reaction formula is as follows:

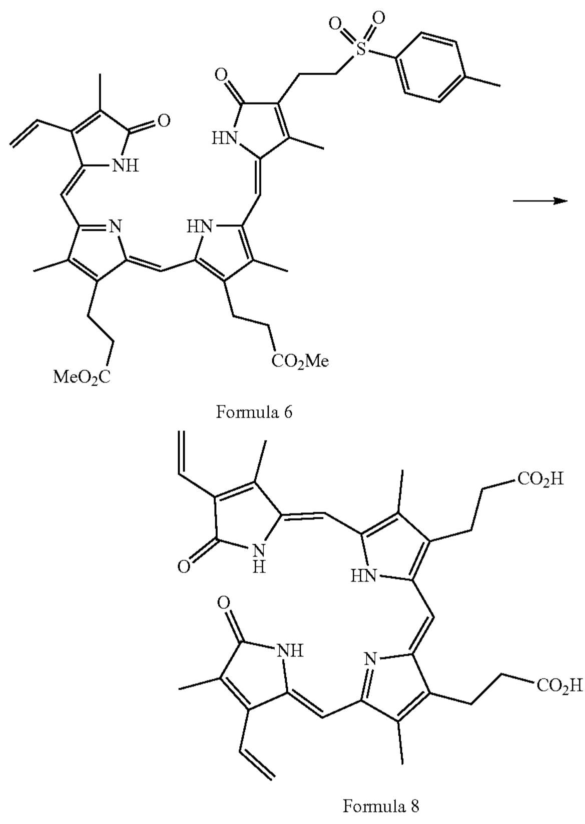

Formula 6

Formula 8

Example 11

1. Synthesis of Compound Represented by Formula 3

Synthesis of 21H-Biline-8,12-dipropanoic acid, 1,19,22,24-tetrahydro-2,7,13,17-tetramethyl-{3,18-bis-[2-[(4-methylphenyl)sulfinyl]ethyl}-1,19-dioxo, 8,12-dimethyl ester (Shown in Formula 3)

1.00 g of 9-tert-butyloxycarbonyl-3,7-dimethyl-8-(2-methoxycarbonyl ethyl)-2-(2-p-tolylene sulfinyl ethyl)-dipyrrolomethen-1-one (shown in Formula 9) was added to 10 mL of trifluoroacetic acid at 20° C. and stirred for 30 min. Thereafter, 0.87 g of 9-formyl-2,7-dimethyl-8-(2-methoxycarbonyl ethyl)-3-(p-toluene sulfinyl ethyl)-dipyrrolomethen-1-one (shown in Formula 10) was added to the resulting mixture, and stirred at 35° C. for 10 hours. 20 mL of dichloromethane was added to the mixed solution. The mixed solution was neutralized with sodium bicarbonate to pH 7. The organic layer was collected, washed with saturated sodium bicarbonate to neutral, dried over anhydrous sodium sulfate, filtered, and recrystallized with ethanol to obtain 1.19 g of a blue-green solid, that is, 21H-Biline-8,12-dipropanoic acid, 1,19,22,24-tetrahydro-2,7,13,17-tetramethyl-{3,18-bis-[2-[(4-methylphenyl)sulfinyl]ethyl}-1,19-dioxo,8,12-dimethyl ester (shown in Formula 3), with a yield of 72%. $^1$H NMR (400 MHz, $CDCl_3$): δ 1.52 (s, 3H), 1.93 (s, 3H), 1.95 (s, 3H), 1.99 (s, 3H), 2.34 (s, 3H), 2.40 (s, 3H), 2.51-2.65 (m, 6H), 2.87 (t, J=7.2 Hz, 2H), 2.96 (t, J=7.2 Hz, 2H), 3.27 (t, J=7.2 Hz, 2H), 3.66 (s, 3H), 3.67 (s, 3H), 5.55 (s, 1H), 5.75 (s, 1H), 6.66 (s, 1H), 7.14 (d, J=8.0 Hz, 2H), 7.30 (d, J=8.0 Hz, 2H), 7.33 (d, J=8.0 Hz, 2H), 7.76 (d, J=8.0 Hz, 2H); ESI-Mass: 891.34 $(M+1)^+$.

The two compounds represented by formulas 9 and 10 are synthesized as follows:

1.1) Synthesis of 9-tert-butyloxycarbonyl-3,7-dimethyl-8-(2-methoxycarbonyl ethyl)-2-(2-p-toluene sulfinyl ethyl)-dipyrrolomethen-1-one (Shown in Formula 9)

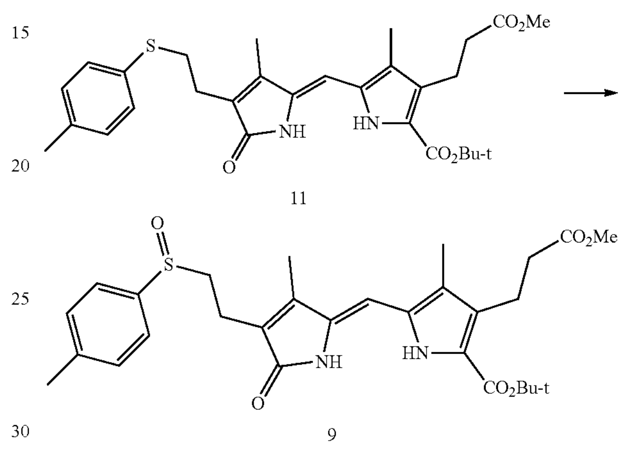

11

9

5.24 g of the compound represented by Formula 11 was put into a reaction flask, dissolved with 30 mL of dichloromethane, and cooled to 0° C. 2.40 g of 85% m-chloro perbenzoic acid was added in batches to the reaction flask, stirred at room temperature for 3 hours, and washed with saturated sodium bisulfite solution. The organic layer was collected, and then washed with saturated salt water, water, dried over anhydrous sodium sulfate, filtered, concentrated to obtain 4.97 g of a yellow solid, that is, 9-tert-butyloxycarbonyl-3,7-dimethyl-8-(2-methoxycarbonyl ethyl)-2-(p-toluene sulfinyl ethyl)-dipyrrolomethen-1-one (shown in Formula 9), with a yield of 92%. The compound can be directly used for next reaction. $^1$H NMR (400 MHz, $CDCl_3$): δ 1.57 (s, 9H), 2.08 (s, 3H), 2.15 (s, 3H), 2.30 (s, 3H), 2.54 (t, J=8.0 Hz, 2H), 2.80 (t, J=7.2 Hz, 2H), 3.03 (t, J=8.0 Hz, 2H), 3.17 (t, J=7.2 Hz, 2H), 3.70 (s, 3H), 6.00 (s, 1H), 7.03 (d, J=8.0 Hz, 2H), 7.23 (d, J=8.0 Hz, 2H), 9.89 (s, 1H), 10.20 (s, 1H); ESI-Mass: 563.25 $(M+Na)^+$.

1.2) Synthesis of 9-tert-butoxycarbonyl-3,7-dimethyl-8-(2-methoxycarbonylethyl)-2-(2-p-toluenesulfoethyl)-dipyrrolidene-1-one (Shown in Formula 11)

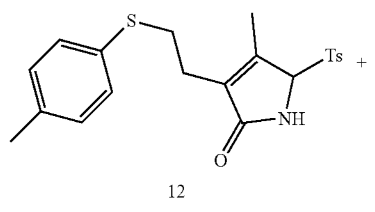

12

-continued

-continued

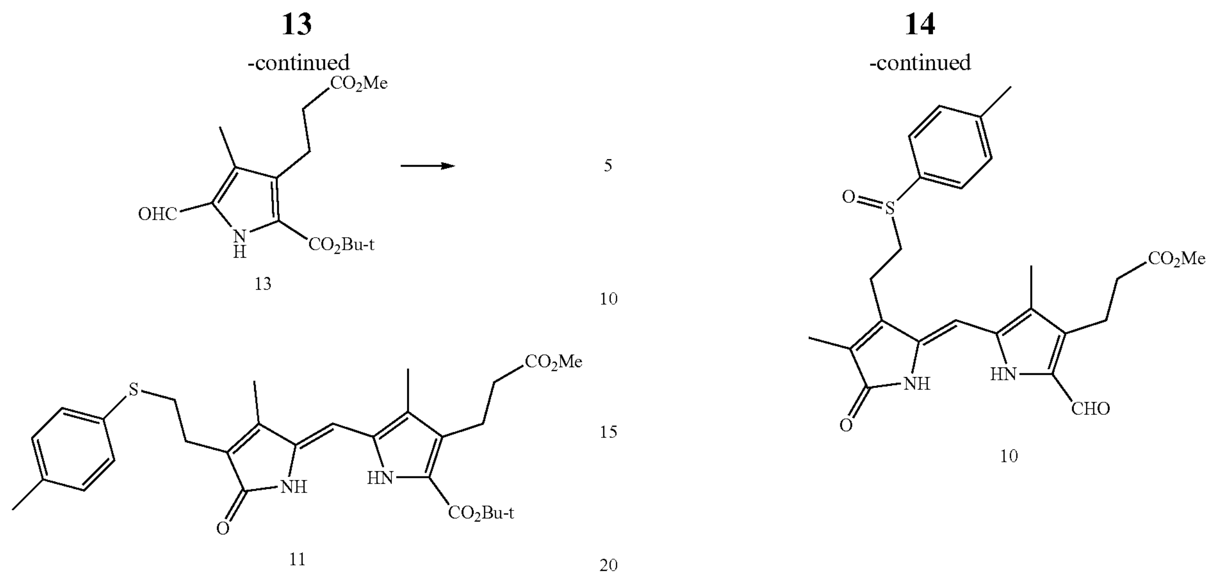

Under nitrogen protection, 10.50 g of the compound having formula 12 and 14.85 g of the compound having formula 13 were mixed and dissolved in 250 mL of anhydrous THF. 16.55 g of tri-n-butylphosphorus and 6.50 g of DBU were sequentially added to the resulting mixture, stirred at room temperature for 12 hours, and then 1.0 g of solid iodine was added. The mixture was further stirred at room temperature for 12 hours and concentrated under reduced pressure. 20 mL of ethanol was added to the residue, to yield a solid. The solid was filtered, and washed with ethanol to obtain 13.60 g of a yellow solid, which is 9-tert butyloxycarbonyl-3,7-dimethyl-8-(2-methoxycarbonyl-ethyl)-2-(2-p-toluenesulfoethyl)-dipyrrolidene-1-one (shown in formula 11), with a yield of 73%. $^1$H NMR (400 MHz, $CDCl_3$): δ 1.56 (s, 9H), 2.07 (s, 3H), 2.13 (s, 3H), 2.28 (s, 3H), 2.54 (t, J=8.1 Hz, 2H), 2.80 (t, J=7.1 Hz, 2H), 3.03 (t, J=8.1 Hz, 2H), 3.15 (t, J=7.1 Hz, 2H), 3.70 (s, 3H), 6.00 (s, 1H), 7.03 (d, J=8.0 Hz, 2H), 7.23 (d, J=8.0 Hz, 2H), 9.89 (s, 1H), 10.18 (s, 1H), 10.71 (s, 1H); ESI-Mass: 446.20 $(M+Na)^+$.

1.3) Synthesis of 9-formyl-2,7-dimethyl-8-(2-methoxycarbonyl ethyl)-2-(2-p-toluene sulfinyl ethyl)-dipyrrolomethen-1-one (Shown in Formula 10)

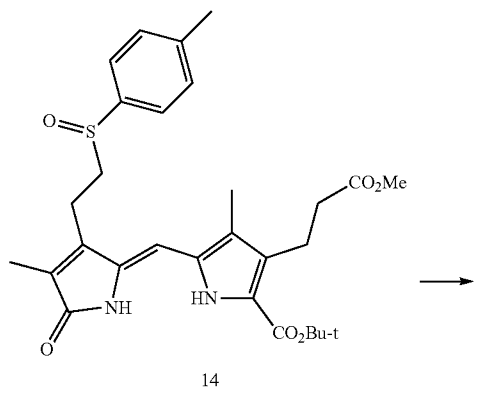

5.00 g (9.3 mmol) of 9-formyl-2,7-dimethyl-8-(2-methoxycarbonyl ethyl)-3-(2-p-toluene sulfinyl ethyl)-dipyrrolidone 1-one (shown in Formula 14) was dissolved in 20 mL of trifluoroacetic acid, stirred at room temperature for 30 minutes, and 20 mL of trimethyl orthoformate was added, continued stirring at room temperature for 1 hour, and then water was added. The resulting mixture was extracted with dichloromethane, washed with saturated sodium bicarbonate to neutral, washed with water, dried with anhydrous sodium sulfate, filtered, concentrated and recrystallized with ethanol to obtain 2.24 g of a yellow solid, namely, 9-formyl-2,7-dimethyl-8-(2-methoxycarbonyl ethyl)-2-(2-p-toluene sulfinyl ethyl)-dipyrrolomethen-1-one (shown in formula 10), with a yield of 55%. $^1$H NMR (400 MHz, $CDCl_3$): δ 1.93 (s, 3H), 2.07 (s, 3H), 2.43 (s, 3H), 2.56 (t, J=7.6 Hz, 2H), 2.66-2.70 (m, 1H), 2.88-2.92 (m, 1H), 2.95-3.10 (m, 4H), 3.65 (s, 3H), 5.98 (s, 1H), 7.34 (d, J=8.0 Hz, 2H), 7.51 (d, J=8.0 Hz, 2H), 9.72 (s, 1H), 10.78 (s, 1H), 10.91 (s, 1H); ESI-Mass: 491.22 $(M+Na)^+$.

2. Synthesis of Compound Represented by Formula 4

Synthesis of 21H-Biline-8,12-dipropanoic acid,3-ethenyl-1,19,22,24-tetrahydro-2,7,13,17-tetramethyl-18-[2-[(4-methylphenyl)sulfinyl]ethyl]-1,19-dioxo,8,12-dimethyl ester (Shown in Formula 4)

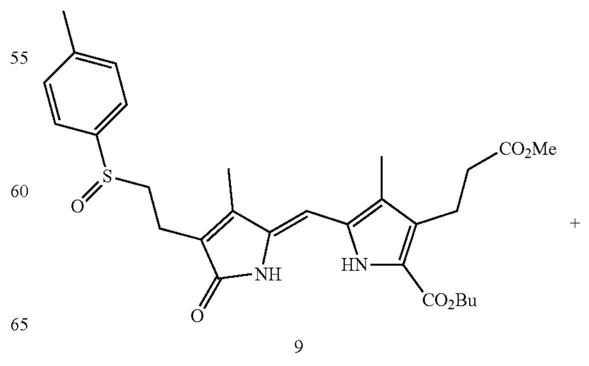

+

-continued

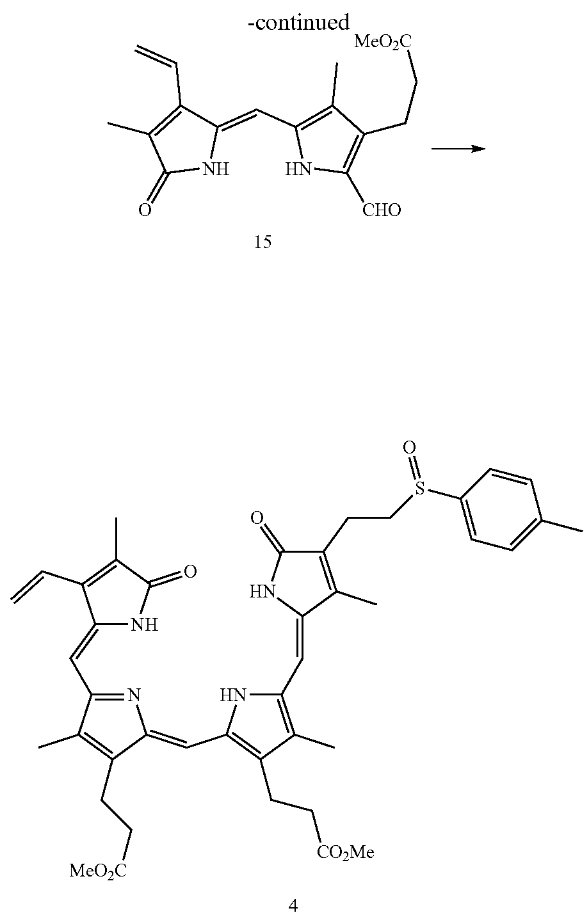

15

4

1.00 g of 9-tert-butyloxycarbonyl-3,7-dimethyl-8-(2-methoxycarbonyl ethyl)-2-(2-p-toluene sulfinyl ethyl)-dipyrrolomethen-1-one (shown in Formula 9) was added to 10 mL of trifluoroacetic acid at 20° C. and stirred for 30 min. Thereafter, 0.617 g of 9-formyl-2,7-dimethyl-8-(2-methoxycarbonylethyl)-3-vinyl dipyrrolidene-1-one (shown in Formula 15) was added to the resulting mixture, and stirred at 35° C. for 10 hours. 20 mL of dichloromethane was added to the mixed solution. The mixed solution was neutralized with sodium bicarbonate to pH 7. The organic layer was collected, washed with saturated sodium bicarbonate to neutral, dried over anhydrous sodium sulfate, filtered, and recrystallized with ethanol to obtain 0.93 g of a blue-green solid, that is, 21H-Biline-8,12-dipropanoic acid,3-ethenyl-1,19,22,24-tetrahydro-2,7,13,17-tetramethyl-18-[2-[(4-methylphenyl)sulfinyl]ethyl]-1,19-dioxo,8,12-dimethyl ester (shown in Formula 4), with a yield of 66%. $^{1}H$ NMR (400 MHz, $CDCl_3$): δ 1.70 (s, 3H), 2.02 (s, 3H), 2.04 (s, 3H), 2.10 (s, 3H), 2.39 (s, 3H), 2.52-2.55 (m, 4H), 2.73-2.78 (m, 2H), 2.86-2.89 (m, 4H), 3.03-3.08 (m, 2H), 3.68 (s, 3H), 5.59 (d, J=17.1, 1H), 5.61 (d, J=10.5, 1H), 5.81 (s, 1H), 5.87 (s, 1H), 6.53 (dd, J=17.1, 11.6 Hz, 1H), 6.65 (s, 1H), 7.29 (d, J=8.2 Hz, 2H), 7.57 (d, J=8.2 Hz, 2H); ESI-Mass: 751.95 $(M+1)^+$.

3. Synthesis of Compound Represented by Formula 5 21H-Biline-8,12-dipropanoic acid, 1,19,22,24-tetrahydro-2,7,13,17-tetramethyl-{3,18-bis-[2-[(4-methylphenyl)sulfonyl]ethyl]}-1,19-dioxo,8,12-dimethyl ester (Shown in in Formula 5)

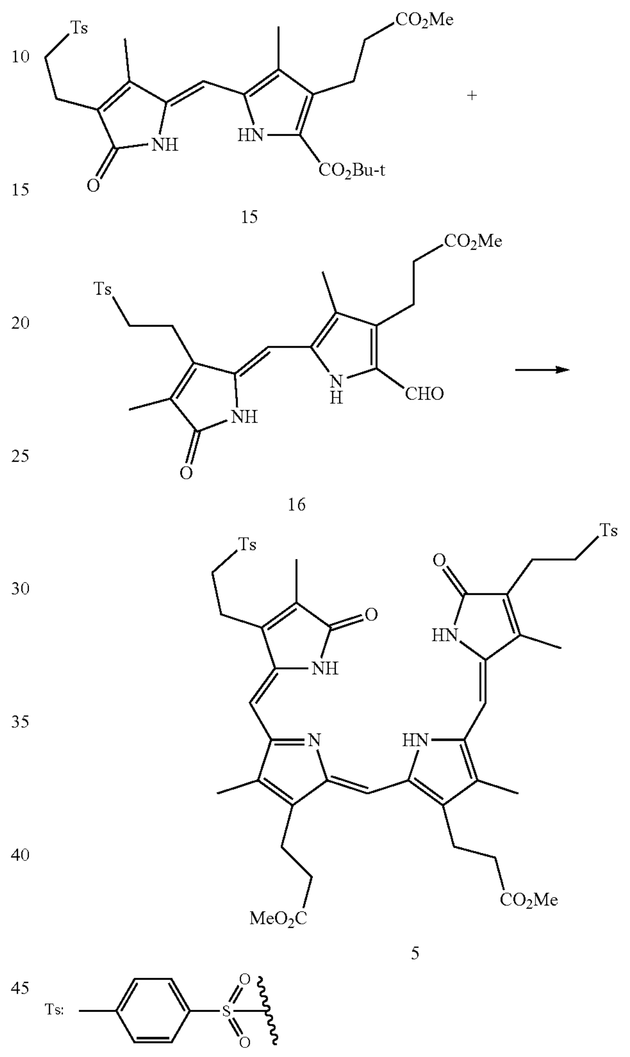

15

+

16

5

1.00 g of 9-formyl-2,7-dimethyl-8-(2-methoxycarbonyl-ethyl)-3-vinyldipyrrolidene-1-one (shown in Formula 15) was dissolved in 5 mL trifluoroacetic acid, stirred at 25° C. for 30 minutes, then 0.87 g of 9-formyl-2,7-dimethyl-8-(2-methoxycarbonyl ethyl)-3-(2-nenenebb p-toluenesulfonyl ethyl)-dipyrrolomethen-1-one was added. The resulting mixture was stirred at 25° C. for 10 hours, concentrated under reduced pressure, dissolved in dichloromethane, washed saturated sodium bicarbonate to neutral. The organic layer was collected, drive over anhydrous sodium sulfate, filtered, and recrystallized with ethanol to obtain 0.91 g of a blue-green solid, with a yield of 55%. $^{1}H$ NMR (400 MHz, $CDCl_3$): δ 1.52 (s, 3H), 1.93 (s, 3H), 1.95 (s, 3H), 1.99 (s, 3H), 2.34 (s, 3H), 2.40 (s, 3H), 2.51-2.65 (m, 6H), 2.87 (t, J=7.2 Hz, 2H), 2.96 (t, J=7.2 Hz, 2H), 3.27 (t, J=7.2 Hz, 2H), 3.66 (s, 3H), 3.67 (s, 3H), 5.55 (s, 1H), 5.75 (s, 1H), 6.66 (s, 1H), 7.14 (d, J=8.0 Hz, 2H), 7.30 (d, J=8.0 Hz, 2H), 7.33 (d, J=8.0 Hz, 2H), 7.76 (d, J=8.0 Hz, 2H); ESI-Mass: 945.34 $(M+Na)^+$.

The two compounds represented by formulas 15 and 16 are synthesized as follows:

2.1) Synthesis of 9-formyl-2,7-dimethyl-8-(2-methoxycarbonyl ethyl)-3-(2-neneneba p-toluene-sulfonyl ethyl)-dipyrrolomethen-1-one (Shown in Formula 16)

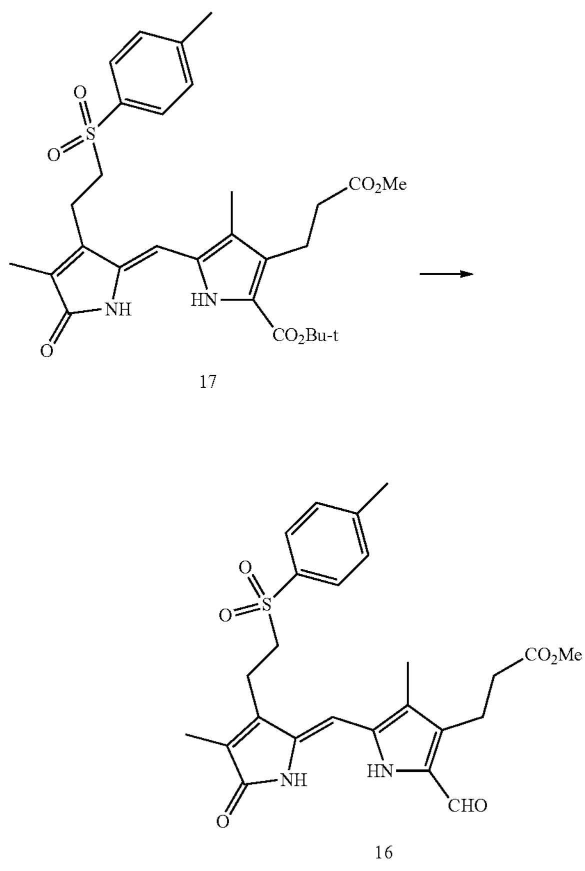

17

16

5.56 g (10.0 mmol) of 9-tert-butyloxycarbonyl-2,7-dimethyl-8-(2-methoxycarbonyl ethyl)-3-p-toluenesulfonyl ethyl)-dipyrrolomethen-1-one (shown in Formula 17) was dissolved in 20 mL of trifluoroacetic acid, stirred at room temperature for 30 minutes, and 20 mL of trimethyl orthoformate was added, continued stirring at room temperature for 1 hour, and then water was added. The resulting mixture was extracted with dichloromethane, washed with saturated sodium bicarbonate to neutral, washed with water, dried with anhydrous sodium sulfate, filtered, concentrated and recrystallized with ethanol to obtain 2.24 g of a yellow solid, namely, 9-formyl-2,7-dimethyl-8-(2-methoxycarbonyl ethyl)-3-p-toluenesulfonyl ethyl)-dipyrrolomethen-1-one (shown in Formula 16), with a yield of 50%. $^{1}H$ NMR (400 MHz, $CDCl_3$): δ 1.93 (s, 3H), 2.07 (s, 3H), 2.43 (s, 3H), 2.56 (t, J=7.6 Hz, 2H), 2.66-2.70 (m, 1H), 2.88-2.92 (m, 1H), 2.95-3.10 (m, 4H), 3.65 (s, 3H), 5.98 (s, 1H), 7.34 (d, J=8.0 Hz, 2H), 7.51 (d, J=8.0 Hz, 2H), 9.72 (s, 1H), 10.78 (s, 1H), 10.91 (s, 1H); ESI-Mass: 507.18 $(M+Na)^+$.

2.2) Synthesis of 9-tert-butoxycarbonyl-2,7-dimethyl-8-(2-methoxycarbonyl ethyl)-3-(2-neneneba p-toluenesulfonyl ethyl)-dipyrrolomethen-1-one (Shown in Formula 17)

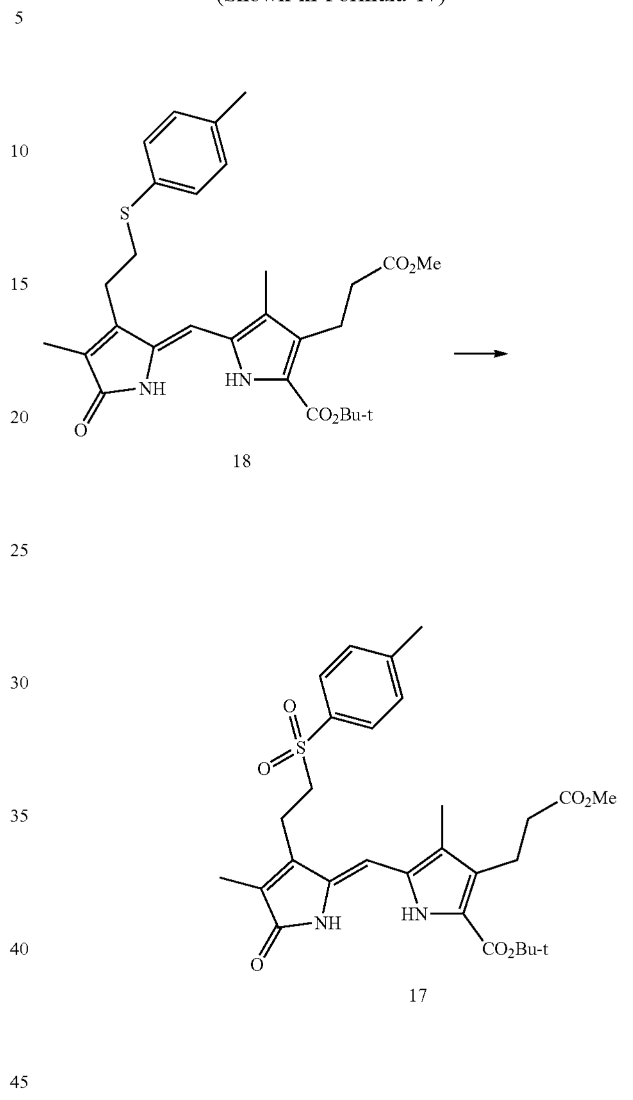

18

17

5. 20 g of 9-tert-butyloxycarbonyl-2,7-dimethyl-8-(2-methoxycarbonyl ethyl)-3-(2-p-tolylene thioethyl)-dipyrrolidone 1-one (shown in Formula 18) was put into a reaction bottle, dissolved with 40 mL of methanol, and then 11 g of 30% m-chloro perbenzoic acid was added. The resulting mixture was stirred at 70° C. for 5 hours, cooled, concentrated under reduced pressure, dissolved in dichloromethane, washed with saturated sodium bisulfite solution. The organic layer was collected, washed with saturated salt water and water in turn, dried over anhydrous sodium sulfate, filtered and concentrated to obtain 5.17 g of a yellow solid, namely 9-tert-butyloxycarbonyl-2,7-dimethyl-8-(2-methoxycarbonyl ethyl)-3-p-toluenesulfonyl ethyl)-dipyrrolomethen-1-one (shown in Formula 17), with a yield of 94%, which can be directly used for next reaction. $^{1}H$ NMR (400 MHz, $CDCl_3$): δ 1.55 (s, 9H), 1.93 (s, 3H), 2.08 (s, 3H), 2.42 (s, 3H), 2.58 (t, J=7.6 Hz, 2H), 2.66-2.71 (m, 1H), 2.87-2.90 (m, 1H), 2.96-3.10 (m, 4H), 3.66 (s, 3H), 5.97 (s, 1H), 7.35 (d, J=8.0 Hz, 2H), 7.53 (d, J=8.0 Hz, 2H), 9.73 (s, 1H), 10.78 (s, 1H), 10.91 (s, 1H); ESI-Mass: 579.32 $(M+Na)^+$.

4. Synthesis of Compound Represented by Formula 6

Synthesis of 21H-Biline-8,12-dipropanoic acid,3-ethenyl-1,19,22,24-tetrahydro-2,7,13,17-tetramethyl-18-[2-[(4-methylphenyl)sulfonyl]ethyl]-1,19-dioxo-8,12-dimethyl ester (Shown in Formula 6)

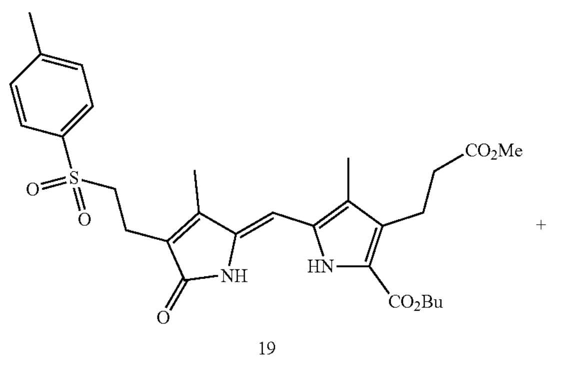

+

19

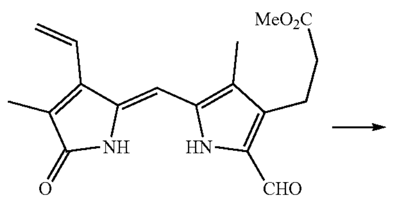

15

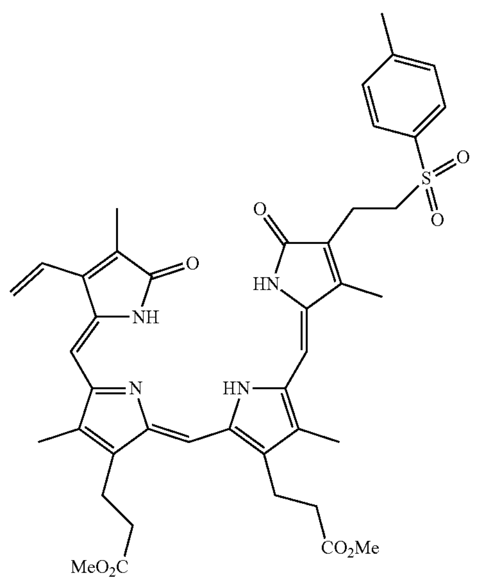

6

1.00 g of 9-tert-butyloxycarbonyl-2,7-dimethyl-8-(2-methoxycarbonyl ethyl)-3-p-toluenesulfonyl ethyl)-dipyrrolomethen-1-one (shown in Formula 17) was added to 10 mL of trifluoroacetic acid at 20° C. and stirred for 30 min. Thereafter, 0.617 g of 9-formyl-2,7-dimethyl-8-(2-methoxycarbonylethyl)-3-vinyldipyrrolidene-1-one (shown in formula 15) was added to the resulting mixture, and stirred at 35° C. for 10 hours. 20 mL of dichloromethane was added to the mixed solution. The mixed solution was neutralized with sodium bicarbonate to pH 7. The organic layer was collected, washed with saturated sodium bicarbonate to neutral, dried over anhydrous sodium sulfate, filtered, and recrystallized with ethanol to obtain 0.93 g of a blue-green solid, that is, 21H-Biline-8,12-dipropanoic acid,3-ethenyl-1,19,22,24-tetrahydro-2,7,13,17-tetramethyl-18-[2-[(4-methylphenyl)sulfonyl]ethyl]-1,19-dioxo-8,12-dimethyl ester (shown in Formula 6), with a yield of 66%.

It will be obvious to those skilled in the art that changes and modifications may be made, and therefore, the aim in the appended claims is to cover all such changes and modifications.

What is claimed is:

1. A method for preparing biliverdin or a derivative thereof, the method comprising:

dissolving a raw material comprising a compound represented by formula 2 in a solvent selected from the group consisting of substituted benzene, pyrrolidone, dimethyl formamide (DMF), and tetrahydrofuran (THF), and a mixture thereof to obtain a resulting mixture:

2

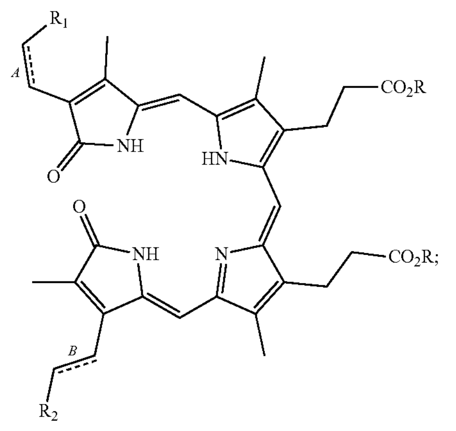

formula 2 wherein:

R is hydrogen, $C_1$-$C_5$ alkyl, or benzyl; "---" at positions A and B independently represent a single bond or a double bond;

when "---" represents a single bond, $R_1$ or $R_2$ connected to the single bond is selected from one of p-toluenesulfonyl, phenylsulfonyl, phenylsulfinyl; and when "---" represents a double bond, $R_1$ or $R_2$ connected to the double bond is hydrogen;

heating the resulting mixture;

removing the solvent to obtain a residue; and extracting the residue to obtain the biliverdin or the derivative thereof, wherein the biliverdin or the derivative thereof is a compound represented by formula 1

1

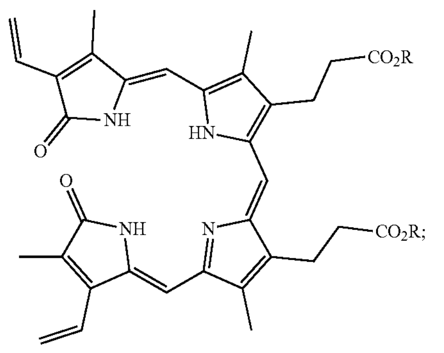

wherein heating the resulting mixture at a temperature of 100-160° C., wherein the biliverdin or the derivative thereof is prepared with the compound represented by formula 2 in the presence of a catalyst, wherein the catalyst is pyridine.

2. The method of claim 1, wherein the compound represented by formula 2 is one of the following compounds:

5

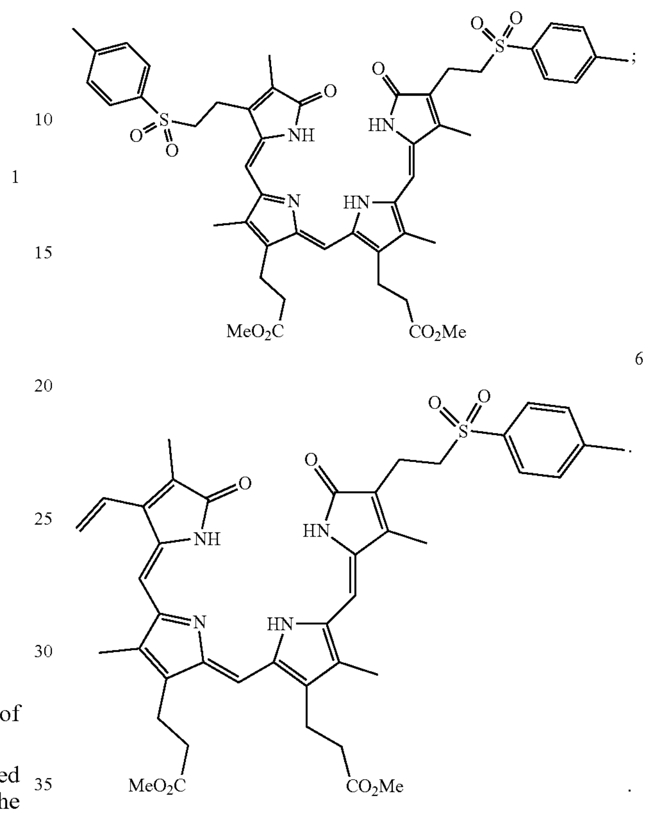

6

.

* * * * *